United States Patent
Pomper et al.

(10) Patent No.: US 10,029,023 B2
(45) Date of Patent: Jul. 24, 2018

(54) THERANOSTIC IMAGING AGENTS AND METHODS OF USE

(75) Inventors: Martin Pomper, Baltimore, MD (US); Zaver Bhujwalla, Baltimore, MD (US); Zhihang Chen, Baltimore, MD (US); Cong Li, Baltimore, MD (US); Sridhar Nimmagadda, Baltimore, MD (US); Marie-France Penet, Baltimore, MD (US); Sangeeta Ray, Ellicott City, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 638 days.

(21) Appl. No.: 14/008,715

(22) PCT Filed: Mar. 30, 2012

(86) PCT No.: PCT/US2012/031396
§ 371 (c)(1),
(2), (4) Date: Feb. 27, 2014

(87) PCT Pub. No.: WO2012/135592
PCT Pub. Date: Oct. 4, 2012

(65) Prior Publication Data
US 2014/0178300 A1    Jun. 26, 2014

Related U.S. Application Data

(60) Provisional application No. 61/470,054, filed on Mar. 31, 2011.

(51) Int. Cl.
| | | |
|---|---|---|
| *A61B 10/00* | (2006.01) |
| *A61B 5/00* | (2006.01) |
| *A61B 8/00* | (2006.01) |
| *A61K 51/08* | (2006.01) |
| *A61K 47/48* | (2006.01) |
| *A61K 49/00* | (2006.01) |
| *A61K 49/12* | (2006.01) |
| *A61K 51/06* | (2006.01) |
| *A61K 9/00* | (2006.01) |
| *C12N 15/113* | (2010.01) |
| *A61K 31/513* | (2006.01) |

(Continued)

(52) U.S. Cl.
CPC .......... *A61K 51/083* (2013.01); *A61K 9/0019* (2013.01); *A61K 31/513* (2013.01); *A61K 31/713* (2013.01); *A61K 38/50* (2013.01); *A61K 47/48138* (2013.01); *A61K 47/48192* (2013.01); *A61K 47/48215* (2013.01); *A61K 47/48315* (2013.01); *A61K 47/48884* (2013.01); *A61K 49/0032* (2013.01); *A61K 49/0054* (2013.01); *A61K 49/126* (2013.01); *A61K 51/065* (2013.01); *C12N 15/113* (2013.01); *C12N 2310/14* (2013.01); *C12N 2310/141* (2013.01); *C12N 2320/30* (2013.01); *C12N 2320/32* (2013.01)

(58) Field of Classification Search
CPC ........ A61K 9/00; A61K 9/0019; A61K 47/00; A61K 47/48138; A61K 47/48192; A61K 47/48215; A61K 47/48315; A61K 47/48884; A61K 49/00; A61K 49/0032; A61K 49/0054; A61K 49/126; A61K 51/00; A61K 51/065; A61K 38/00; A61K 38/50; A61K 51/083; A61K 31/00; A61K 31/513; A61K 31/713; A61K 38/005; A61K 49/0017; A61K 49/0004; A61K 2123/00; A61K 2121/00; C12N 2310/14; C12N 2310/141; C12N 2320/30; C12N 2320/32
USPC .......... 424/1.11, 1.49, 1.65, 1.73, 1.81, 1.85, 424/1.89, 9.1, 9.2, 9.3, 9.4, 9.5, 9.6; 514/1, 1.1, 19.2, 19.3, 19.4, 19.5, 19.6; 534/7, 10–16; 530/300
See application file for complete search history.

(56) References Cited

U.S. PATENT DOCUMENTS

| | | | | |
|---|---|---|---|---|
| 2006/0275371 A1* | 12/2006 | Dai | .................. | A61K 47/48869 424/489 |
| 2011/0044893 A1* | 2/2011 | Schnitzer | ........... | A61K 38/1709 424/1.11 |

FOREIGN PATENT DOCUMENTS

WO    2010108125 A2    9/2010

OTHER PUBLICATIONS

Oh et al, Advance Drug Delivery Reviews, 2009, vol. 61, pp. 850-862.*

(Continued)

*Primary Examiner* — D L Jones
(74) *Attorney, Agent, or Firm* — Casimir Jones, S.C.; Jeffrey W. Childers

(57) ABSTRACT

The present invention provides targeted nanoplex molecules which carry multimodality imaging reporters together with target enzyme inhibitors such as siRNAs and target prodrug enzymes, that are useful for theranostic imaging of cells and diseases, including, for example, various cancers, and including metastatic prostate cancer. The nanoplex molecules of the present invention provide a platform technology toward many cancer subtypes and alternative therapeutic targets. Downregulation of specific pathways using targeted enzyme inhibitors further provides unique opportunities to target cancer cells selectively while sparing normal tissue. The nanoplex molecule platform described herein has the ability to deliver multiple siRNA enzyme inhibitors. Methods of diagnosis and treatment of various diseases are also included. The strategy described herein can be useful to down-regulate multi-drug resistance pathways, or repair enzymes with the goal of increasing the efficacy, safety, and efficiency of chemotherapeutic or irradiation therapies.

13 Claims, 11 Drawing Sheets

(51) Int. Cl.
*A61K 31/713* (2006.01)
*A61K 38/50* (2006.01)

(56) References Cited

OTHER PUBLICATIONS

Li et al, American Chemical Society Nano, 2010, vol. 4, No. 11, pp. 6707-6716.*
International Search Report dated Feb. 2, 2013 for corresponding PCT International Patent Application No. PCT/US2012/031396.
Banerjee et al., J. Med. Chem. vol. 51, pp. 4504-4517, 2008.
Turner et al., 1987, CSH Symp. Quant. Biol. LII pp. 123-133.
Frier et al., 1986, Proc. Nat. Acad. Sci. USA 83:9373-9377.
Turner et al., 1987, J. Am. Chem. Soc. 109:3783-3785.
Kozikowski et al., "Design of Remarkably Simple, Yet Potent Urea-Based Inhibitors of Glutamate Carboxypeptidase II (NAALADase)", J.Med. Chem., 2004 44:298-301.
Glunde et al., "RNA Interference-Mediated Choline Kinase Suppression in Breast Cancer Cells Induces Differentiation and Reduces Proliferation", Cancer Res., 2005 65: 11034-43.
Mease et al., "N-[N-[(S)-1,3-Dicarboxypropyl]Carbamoyl]-4-[18F]Fluorobenzyl-LCysteine, [18F]DCFBC: A New Imaging Probe for Prostate Cancer", Clin. Cancer Res., 2008 14:3036-43.

* cited by examiner

Total choline density maps

Pre-treatment         48 h post-treatment

THERANOSTIC IMAGING AGENTS AND METHODS OF USE

REFERENCE TO RELATED APPLICATIONS

This application is a 35 U.S.C. § 371 U.S. national phase entry of International Application No. PCT/US2012/031396 having an international filing date of Mar. 30, 2012, which claims the benefit of U.S. Provisional Application No. 61/470,054, filed Mar. 31, 2011, the content of each of the aforementioned applications is herein incorporated by reference in its entirety.

STATEMENT OF GOVERNMENTAL INTEREST

This invention was made with U.S. government support under NIH grant nos. P50 CA103175, R01CA138515, U54 CA151838, and R01 CA134675. The U.S. government has certain rights in the invention.

BACKGROUND OF THE INVENTION

Combining advances in nanotechnology with molecular biology and imaging is providing exciting new nanomedicine-based strategies for cancer treatment. The ideal cancer therapy would target cancer cells while sparing normal tissue. In most conventional chemotherapies, normal cells are damaged together with cancer cells. siRNA-mediated silencing of specific targets has significant potential in cancer therapy to down-regulate pathways that are up-regulated in cancer cells but not in normal tissue to achieve cancer cell-specific treatment. Similarly, prodrug enzyme therapy, where a drug-activating enzyme delivered to the tumor converts a nontoxic prodrug to a cytotoxic drug, is being actively investigated to minimize normal tissue damage. A combination of both strategies can be exploited to enhance the effect of conventional chemotherapy against cancer cells and minimize damage to normal tissue. Imaging can play a key role in several aspects of such a treatment. Since tumor vasculature is typically heterogeneous and chaotic, the ability to image the delivery of the siRNA and the prodrug-activating enzyme within the tumor would ascertain effective delivery. Noninvasive detection of target down-regulation and visualization of the prodrug-activating enzyme could be exploited to time prodrug administration to minimize normal tissue damage. Detecting the conversion of the prodrug to the active drug within the tumor would verify that the prodrug enzyme was functional.

Prostate cancer (PC) is the second leading cause of death from cancer in men in the United States. The vast majority of men dying of PC succumb to metastatic androgen refractory disease. There is therefore a compelling need to find effective treatments for metastatic PC. In theranostics, noninvasive imaging-based detection of a target is combined with the delivery of a therapeutic payload to the target.

There still exists, therefore, a need for targeted therapy of cancers, including metastatic prostate cancer.

SUMMARY OF THE INVENTION

In accordance with an embodiment, the present invention provides a nanoplex molecule comprising a) a prodrug enzyme portion, b) a reporter portion, c) an enzyme inhibitor portion and d) a targeting agent.

In accordance with another embodiment, the present invention provides a nanoplex molecule comprising a prodrug portion, a reporter portion, an enzyme portion and a targeting agent, wherein, the prodrug enzyme portion comprises an enzyme, the reporter portion comprises a poly-L-lysine carrier linked to a dye and a chelating agent labeled with a radioisotope linked to a polyethyleneimine (PEI): polyethylene glycol (PEG) graft co-polymer, and the targeting agent binds a target cell membrane protein with high affinity.

In accordance with a further embodiment, the present invention provides a pharmaceutical composition comprising one or more nanoplex molecules as described herein, and a pharmaceutically acceptable carrier.

In accordance with still another embodiment, the present invention provides a pharmaceutical composition comprising one or more nanoplex molecules as described herein, a second therapeutic agent, and a pharmaceutically acceptable carrier.

In accordance with yet a further embodiment, the present invention provides a method of modulating expression of a target gene in a host cell or population of cells comprising administering to the cell or population of cells one or more nanoplex molecules as described herein, or the pharmaceutical composition comprising one or more nanoplex molecules, in an amount sufficient to modulate target gene expression with the host cell or population of cells.

In accordance with another embodiment, the present invention provides a use of the nanoplex molecules described herein, in an effective amount, to prepare a medicament, preferably for use as a medicament for treating a disease in a subject.

DETAILED DESCRIPTION OF THE INVENTION

Figure 1A:
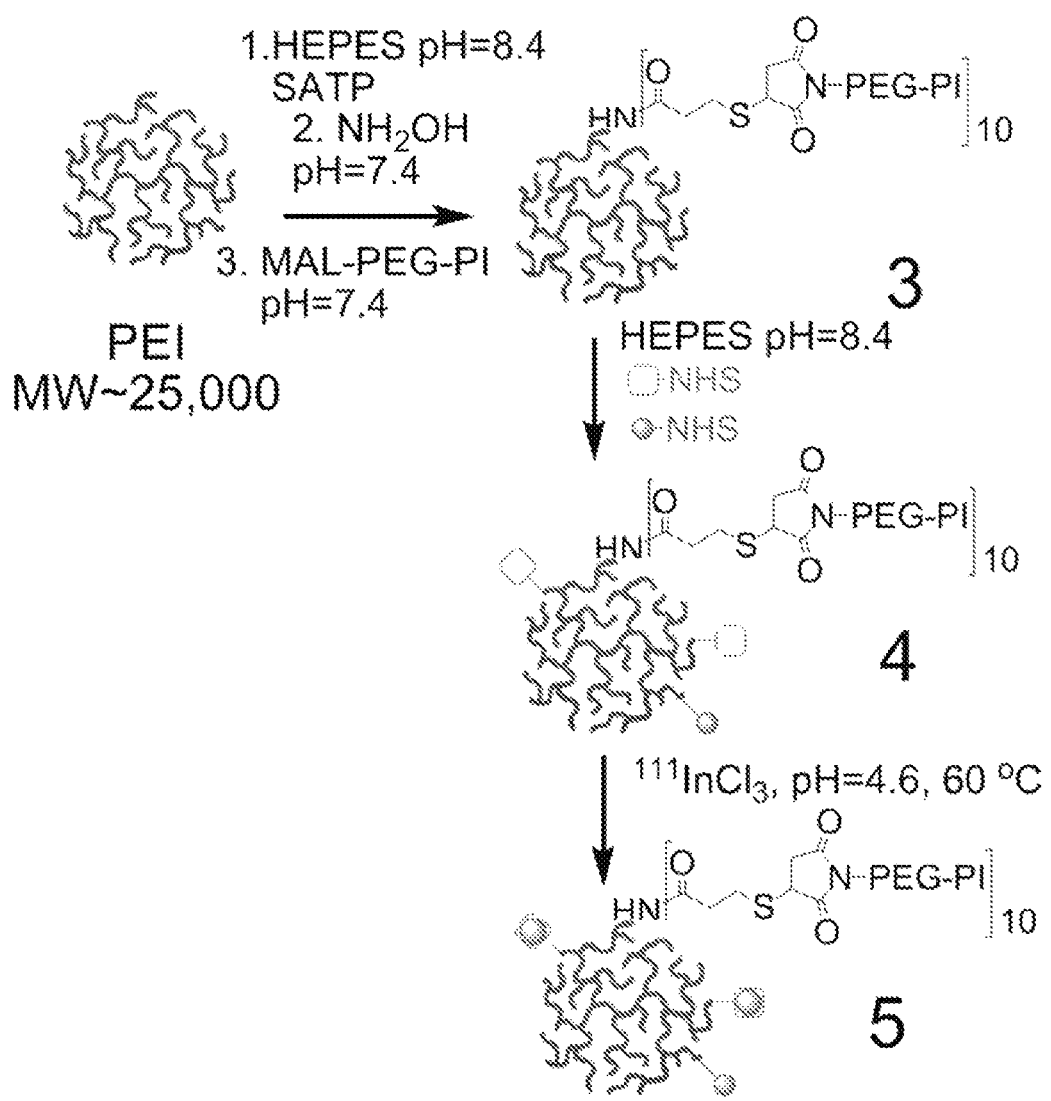
FIGS. 1A-1C illustrate the general synthetic procedure of an embodiment of the nanoplex molecules of the present invention.

A therapeutic nanoplex molecule of the present invention containing multi-modal imaging reporters can be useful for targeting a specific cell type or population of cells. The nanoplex molecules of the present invention are useful in identifying target cells of interest, such as cancer cells, and delivering to the target cell an imaging reporter, as well as a enzyme which is functional in the target cell cytosol, and an enzyme inhibitor, which is a polyribonucleotide which modulates the expression of a target gene in the target cell.

In one embodiment, a nanoplex molecule was targeted to prostate-specific membrane antigen (PSMA), which is expressed on the cell surface of castrate-resistant PC. The nanoplex molecule was designed to deliver small interfering RNA (siRNA) along with a prodrug enzyme to PSMA-expressing tumors. Each component of the nanoplex molecule was carefully selected to evaluate its diagnostic aspect of PSMA imaging, and its therapeutic aspects of siRNA-mediated down-regulation of a target gene and the conversion of a prodrug to cytotoxic drug, using noninvasive multi-modality imaging.

In accordance with an embodiment, the present invention provides a nanoplex molecule comprising a) a prodrug enzyme portion, b) a reporter portion, c) an enzyme inhibitor portion and d) a targeting agent.

As used herein, the term "prodrug enzyme portion" means that this specific portion of the nanoplex molecule comprises a functional enzyme or functional portion thereof, which is retains its activity in the cytosol of the target cell or population of cells. It will be understood by those of ordinary skill that the enzyme or functional portion thereof, can be any enzyme of interest. In accordance with an embodiment, the enzyme has an activity which converts a prodrug molecule into an active drug molecule. The enzyme can be any which will effect this conversion of the prodrug molecule. The enzyme will preferably be otherwise non-toxic to the target cell, and may or may not already be expressed in the target cell. Non-limiting examples of the types of enzyme which is encompassed by the prodrug enzyme include kinases, phosphatases, deaminases, acetylases, and others.

In an embodiment of the present invention, the prodrug enzyme is bacterial cytosine deaminase. When the enzyme is functional in the cytosol of the target cell, 5-fluorocytosine (5-FC), which is non-toxic, can be administered to the cell or population of cells. Only the cells which take up the nanoplex molecules, will convert the 5-FC into 5-fluorouracil (5-FU) which inhibits DNA synthesis and is a cytotoxic agent.

As used herein, the term "reporter portion" means that this specific portion of the molecule comprises at least two imaging agents which are attached to the nanoplex molecule. At least one of the imaging agents is a fluorescent dye. The dyes may be emitters in the visible or near-infrared (NIR) spectrum. Known dyes useful in the present invention include carbocyanine, indocarbocyanine, oxacarbocyanine, thüicarbocyanine and merocyanine, polymethine, coumarine, rhodamine, xanthene, fluorescein, borondipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

Organic dyes which are active in the NIR region are known in biomedical applications. However, there are only a few NIR dyes that are readily available due to the limitations of conventional dyes, such as poor hydrophilicity and photostability, low quantum yield, insufficient stability and low detection sensitivity in biological system, etc. Significant progress has been made on the recent development of NIR dyes (including cyanine dyes, squaraine, phthalocyanines, porphyrin derivatives and BODIPY (borondipyrromethane) analogues) with much improved chemical and photostability, high fluorescence intensity and long fluorescent life. Examples of NIR dyes include cyanine dyes (also called as polymethine cyanine dyes) are small organic molecules with two aromatic nitrogen-containing heterocycles linked by a polymethine bridge and include Cy5, Cy5.5, Cy7 and their derivatives. Squaraines (often called Squarylium dyes) consist of an oxocyclobutenolate core with aromatic or heterocyclic components at both ends of the molecules, an example is KSQ-4-H. Phthalocyanines, are two-dimensional 18π-electron aromatic porphyrin derivatives, consisting of four bridged pyrrole subunits linked together through nitrogen atoms. BODIPY (boron-dipyrromethane) dyes have a general structure of 4,4'-difluoro-4-bora-3a,4a-diaza-s-indacene) and sharp fluorescence with high quantum yield and excellent thermal and photochemical stability.

Other imaging agents which are attached to the nanoplex molecules of the present invention include PET and SPECT imaging agents. The most widely used agents include branched chelating agents such as di-ethylene tri-amine penta-acetic acid (DTPA), 1,4,7,10-tetra-azacyclododecane-1,4,7,10-tetraacetic acid (DOTA) and their analogs. Chelating agents, such as di-amine dithiols, activated mercaptoacetyl-glycyl-glycyl-gylcine (MAG3), and hydrazidonicotinamide (HYNIC), are able to chelate metals like $^{99m}$Tc and $^{186}$Re. Instead of using chelating agents, a prosthetic group such as N-succinimidyl-4-$^{18}$F-fluorobenzoate ($^{18}$F-SFB) is necessary for labeling peptides with $^{18}$F. In accordance with a preferred embodiment, the chelating agent is DOTA.

In accordance with an embodiment, the present invention provides a nanoplex molecule wherein the reporter portion comprises a metal isotope suitable for imaging. Examples of isotopes useful in the present invention include Tc-94m, Tc-99m, In-111, Ga-67, Ga-68, Y-86, Y-90, Lu-177, Re-186, Re-188, Cu-64, Cu-67, Co-55, Co-57, Sc-47, Ac-225, Bi-213, Bi-212, Pb-212, Sm-153, Ho-166, or Dy-i66.

In accordance with an embodiment, the present invention provides a nanoplex molecule wherein the reporter portion comprises $^{111}$In labeled DOTA which is known to be suitable for use in SPECT imaging.

In accordance with another embodiment, the present invention provides a nanoplex molecule wherein the reporter portion comprises $Gd^{3+}$ labeled DOTA which is known to be suitable for use in MR imaging. It is understood by those of ordinary skill in the art that other suitable radioisotopes can be substituted for $^{111}$In and $Gd^{3+}$ disclosed herein.

In accordance with an embodiment, the reporter portion of the present invention comprises a polyethyleneimine (PEI):polyethylene glycol (PEG) graft copolymer, wherein the one or more DOTA moieties and/or rhodamine molecules are attached to the PEI:PEG copolymer.

In accordance with an embodiment, the reporter portion of the present invention also comprises a poly-L-lysine (PLL) polymer, wherein the NIR dye is attached thereto. The PLL polymer is linked to the PEI:PEG copolymer by a linker molecule. For instance linking groups having alkyl, aryl, combination of alkyl and aryl, or alkyl and aryl groups having heteroatoms may be present. For example, the linker can be a $C_1$-$C_{20}$ alkyl, $C_2$-$C_{20}$ alkenyl, $C_2$-$C_{20}$ alkynyl, $C_1$-$C_{20}$ hydroxyalkyl, $C_1$-$C_{20}$ alkoxy, $C_1$-$C_{20}$ alkoxy $C_1$-$C_{20}$ alkyl, $C_1$-$C_{20}$ alkylamino, di-$C_1$-$C_{20}$ alkylamino, $C_1$-$C_{20}$ dialkylamino $C_1$-$C_{20}$ alkyl, $C_1$-$C_{20}$ thioalkyl, $C_2$-$C_{20}$ thioalkenyl, $C_2$-$C_{20}$ thioalkynyl, $C_6$-$C_{22}$ aryloxy, $C_6$-$C_{22}$ arylamino $C_2$-$C_{20}$ acyloxy, $C_2$-$C_{20}$ thioacyl, $C_1$-$C_{20}$ amido, and $C_1$-$C_{20}$ sulphonamido.

As used herein, the term "enzyme inhibitor portion" means that portion of the nanoplex molecule which has a function as an inhibitor of a target enzyme in the target cell or population of cells. In an embodiment, the enzyme inhibitor portion can include any small molecule suitable for use in modulating or inhibiting the normal function of the target enzyme in the target cell. Examples of small molecules, without limitation, include small organic molecules, peptides, oligonucleotides, aptamers, antibodies, and siRNAs. In accordance with an embodiment, the enzyme inhibitor portion comprises a siRNA.

It will be understood that the choice of enzyme as the target for the inhibitor is well within the skill of those in the art. Typical choices for enzymes to target for inhibition are those which increase cytotoxicity in the target cell or population of cells. Examples of types of enzyme targets include, for example, enzymes used in DNA synthesis, replication or repair, protein synthesis, enzymes which are upregulated in target cell populations, cell signaling and cell metabolic control. Examples of specific enzyme targets include dihydrofolate reductase, difluoromethylornithine, and RNA and DNA polymerases. In accordance with an embodiment, the enzyme inhibitor portion is specific for choline kinase (Chk). In an embodiment, the present invention provides an enzyme inhibitor portion comprising a siRNA directed to Chk.

In accordance with the invention, in an embodiment, the siRNA enzyme inhibitor is associated with the PEI:PEG graft copolymer via electrostatic interaction of the siRNA with the copolymer.

As used herein, the term "targeting agent" means that portion of the nanoplex molecule which is capable of binding with high affinity to a target membrane protein on a target cell or population of cells. Examples of the targeting agent of the present invention include, for example, small organic molecules, peptides, oligonucleotides, aptamers, antibodies known to bind with high affinity to specific membrane proteins. Target membrane proteins are those known to be expressed in target cells. Typically, the target membrane proteins will be preferentially expressed on target cells vs. normal or non-target tissue or upregulated in target cells when compared with non-target cells. Examples of receptor targets include, but are not limited to ACPP (acid phosphatase, prostate phosphatase) ADAM10 (ADAM metaliopeptidase domain 10), Peptidase ADAM 15 (ADAM metallopeptidase domain 15 Peptidase), FN 1 (Fibronectin 1), FOLH1 (Prostate-specific membrane antigen 1), Peptidase GNA12 (Guanine nucleotide-binding protein alpha 12), HRAS (Harvey rat sarcoma viral oncogene homolog Enzyme), KLK3 (Kallikrein-related peptidase 3 Peptidase), MMP3 (Matrix metaliopeptidase 3 Peptidase), MMP13 (Matrix metaliopeptidase 13 Peptidase), OCLN (Occludin Enzyme), SILV (Silver homolog (mouse) Enzyme), Integrins, VEGFs (Vascular Endothelial Growth Factor), VEGFR-1 (Vascular Endothelial Growth Factor receptor 1), VEGFR-2, TGF-α (Transforming growth factor-α) PDGF (Platelet derived growth factor), and others.

In accordance with an embodiment, the targeting agent of the nanoplex molecule can be directed to target cells, such as cancer cells. Examples of prostate specific targeting agents include those identified in international patent publication No. WO2010/108125, and incorporated by reference herein.

In an embodiment, the target cell is castrate resistant PC, which express PSMA, and the targeting agent is (2-(3-[1-carboxy-5-[7-(2,5-dioxo-pyrrolidin-1-yloxycarbonyl)-heptanoylamino]-pentyl]-ureido)-pentanedioic acid, which binds PSMA with high affinity (*J. Med. Chem.*, 2004 44:298-301). Other agents which bind PSMA can also be used including, for example those found in (*Clin. Cancer Res.*, 2008 14:3036-43). Often, the compounds are prepared by sequentially adding components to a preformed urea, such as the lysine-urea-glutamate compounds described in Banerjee et al. (*J. Med. Chem.* vol. 51, pp. 4504-4517, 2008). Other urea-based compounds may also be used as building blocks.

Compounds are assembled by reactions between different components, to form linkages such as ureas (—NRC(O)NR—), thioureas (—NRC(S)NR—), amides (—C(O)NR— or —NRC(O)—), or esters (—C(O)O— or —OC(O)—). Urea linkages may be readily prepared by reaction between an amine and an isocyanate, or between an amine and an activated carbonamide (—NRC(O)—). Thioureas may be readily prepared from reaction of an amine with an isothiocyanate. Amides (—C(O)NR— or —NRC(O)—) may be readily prepared by reactions between amines and activated carboxylic acids or esters, such as an acyl halide or N-hydroxysuccinimide ester. Carboxylic acids may also be activated in situ, for example, with a coupling reagent, such as a carbodiimide, or carbonyldiimidazole (CDI). Esters may be formed by reaction between alcohols and activated carboxylic acids. Triazoles are readily prepared by reaction between an azide and an alkyne, optionally in the presence of a copper (Cu) catalyst.

Protecting groups may be used, if necessary, to protect reactive groups while the compounds are being assembled. Suitable protecting groups, and their removal, will be readily available to one of ordinary skill in the art.

In this way, the compounds may be easily prepared from individual building blocks, such as amines, carboxylic acids, and amino acids.

In accordance with an embodiment, the present invention provides a nanoplex molecule comprising a prodrug portion, a reporter portion, an enzyme portion and a targeting agent, wherein, the prodrug enzyme portion comprises an enzyme, the reporter portion comprises a poly-L-lysine carrier linked to a NIR dye and a DOTA moiety labeled with either $^{111}$In or $Gd^{3+}$ linked to a PEI:PEG co-polymer; and the targeting agent binds a target cell membrane protein with high affinity. In an embodiment, the prodrug enzyme portion comprises the enzyme bacterial cytosine deaminase (bCD).

In another embodiment, the reporter portion comprises a poly-L-lysine carrier linked to Cy5.5 dye.

In a further embodiment, the reporter portion comprises a DOTA moiety labeled with $^{111}$In linked to a PEI:PEG co-polymer.

In yet another embodiment, the reporter portion comprises a DOTA moiety labeled with $Gd^{3+}$ linked to a PEI:PEG co-polymer.

In another embodiment, the targeting agent is a small molecule or antibody specific for a target cell membrane protein of interest. In a further embodiment, the target cell membrane protein of interest is PSMA.

In an embodiment of the present invention, a small molecule was used based on the glutamate-urea-X (X is an α-amino acid derivative) motif to achieve PSMA-specific retention of nanoplex 1 through electrostatic interaction with the extracellular active site of PSMA. The three carboxylic acid groups of the PSMA targeting moiety are necessary for binding with PSMA, with the urea providing interaction with $Zn^{2+}$ at the active site. In addition, a 3.4 KD PEG chain is added to separate the targeting moiety from the nanoplex, since the targeting moiety should reach deep within PSMA for productive binding. The PEG chain can be any suitable length. In accordance with an embodiment, the PEG chain can have a length of about 1 KD to about 5 KD, preferable between about 2 KD to about 4 KD in length.

In yet another embodiment, the targeting agent is (2-(3-[1-carboxy-5-[7-(2,5-dioxo-pyrrolidin-1-yloxycarbonyl)-heptanoylamino]-pentyl]-ureido)-pentanedioic acid.

In an embodiment, the enzyme inhibitor of the nanoplex molecule is specific for an enzyme which is overexpressed in a target cell. In another embodiment, the target cell is a cancer cell, preferably a prostate cancer cell, and more preferably, a castrate-resistant prostate cancer cell.

In a further embodiment, the enzyme inhibitor portion comprises at least one polyribonucleotide molecule. In still another embodiment, the at least one polynucleotide molecule is selected from the group consisting of: single stranded RNA, double stranded RNA, micro-RNA (miRNA), short-hairpin RNA (shRNA), siRNA, and/or RNA analogs thereof.

In still a further embodiment, the enzyme inhibitor inhibits the choline kinase (Chk) enzyme, and the enzyme inhibitor is a siRNA specific for Chk.

In accordance with an embodiment, the present invention provides a pharmaceutical composition comprising one or more nanoplex molecules described herein and a pharmaceutically acceptable carrier.

In another embodiment, the present invention provides a pharmaceutical composition comprising one or more nanoplex molecules described herein, a pharmaceutically active compound, and a pharmaceutically acceptable carrier.

In accordance with an embodiment, the present invention provides a method of modulating expression of a target gene in a host cell or population of cells comprising administering to the cell or population of cells the nanoplex molecules described herein, or the pharmaceutical composition described herein, in an amount sufficient to modulate target gene expression with the host cell or population of cells.

In another embodiment, the target gene is upregulated in a cancer cell when compared to a non-cancerous cell.

In accordance with an embodiment, the present invention provides a use of the nanoplex molecule described herein, in an effective amount, to prepare a medicament, preferably for use as a medicament for treating a disease in a subject.

In another embodiment, the medicament further comprises a pharmaceutically acceptable carrier.

In a further embodiment, the medicament further comprises a second therapeutic agent. In still another embodiment, the disease is cancer, and in a preferred embodiment, the disease is castrate-resistant prostate cancer.

As used herein, the term "polymers, co-polymers and derivatives" will be understood by those of ordinary skill in the art. Polycationic block and graft copolymers and their derivatives, can also be used in the nanoplex, and include, for example, polyethylene glycol polymers. Examples of block copolymers useful in the present invention include, PEI:PEG, and derivatives thereof.

Furthermore, it is understood that various embodiments comprising two or more different polycationic polymers can be used to produce the nanoplex molecules of the present invention.

As used herein, the polycationic polymers, including linear and branched polymers, as well as the block and graft copolymers used in various embodiments of the present invention, are derivatives of polycationic polymers that include biocompatible polymers (that is, polymers that do not cause significant undesired physiological reactions), that can be either biodegradable or non-biodegradable polymers or blends or copolymers thereof.

The term "biodegradable" as used herein, refers to degradation in a biological system, for example enzymatic degradation or hydrolytic degradation.

The term "polynucleotide," as used herein, includes and/or is synonymous with "nucleic acid," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

The term "polyribonucleotide," as used herein, includes "ribonucleic acid," "oligoribonucleotide," and "ribonucleic acid molecule," and generally means a polymer of RNA which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It may be suitable in some instances, in an embodiment, for the nucleic acids to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

In another embodiment, the present invention provides one or more nanoplex molecules, wherein the polyribonucleotide molecule is selected from the group consisting of single stranded RNA, double stranded RNA, micro-RNA (miRNA), short-hairpin RNA (shRNA), and/or analogs thereof.

The polyribonucleotides incorporated within the nanoparticles of the present invention can comprise any nucleotide sequence that encodes for a target gene of interest. In an embodiment, the present invention provides that the polynucleotide encodes for a complementary sequence to a target mRNA sequence of a target gene of interest in a cell or population of cells, either in vitro, or in vivo in a host. In another embodiment, the polynucleotide is an isolated or purified nucleic acid comprising a nucleotide sequence which is complementary to the nucleotide sequence of any target nucleotide sequence or a nucleotide sequence which hybridizes under stringent conditions to the nucleotide sequence of any of the nucleic acids described herein.

The present invention also relates to compounds, compositions, and methods useful for modulating the expression and activity of a target gene of interest, or expression and/or activity by RNAi using small nucleic acid molecules. As used herein, the instant invention features small nucleic acid molecules, or polyribonucleotides, and includes terms such as such as siRNA, siNA, dsRNA, miRNA, and shRNA molecules and methods used to modulate the expression of target genes of interest.

A polyribonucleotide of the invention can be unmodified or chemically modified. A polyribonucleotide of the instant invention can be chemically synthesized, expressed from a vector or enzymatically synthesized. The instant invention also features various chemically modified polyribonucleotides, including, for example, siRNA molecules capable of modulating repeat expansion gene expression or activity in cells by RNAi. The use of chemically modified siRNA improves various properties of native siRNA molecules through increased resistance to nuclease degradation in vivo and/or through improved cellular uptake.

In one embodiment, the polyribonucleotide molecule of the present invention comprises modified nucleotides while maintaining the ability to mediate RNAi. The modified nucleotides can be used to improve in vitro or in vivo characteristics, such as stability, activity, and/or bioavailability. For example, when the polyribonucleotide molecule is a siRNA molecule, the invention can comprise modified nucleotides as a percentage of the total number of nucleotides present in the siRNA molecule. As such, an siRNA molecule of the invention can generally comprise about 5% to about 100% modified nucleotides (e.g., 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siRNA molecule will depend on the total number of nucleotides present in the siRNA. If the siRNA molecule is single-stranded, the percent modification can be based upon the total number of nucleotides present in the single-stranded siRNA molecules. Likewise, if the siRNA molecule is double-stranded, the percent modification can be based upon the total number of nucleotides present in the sense strand, antisense strand, or both the sense and antisense strands.

The term "modulate," as used herein means that the expression of the target gene, or level of RNA molecule or equivalent RNA molecules encoding one or more target proteins or protein subunits, or activity of one or more proteins or protein subunits is up regulated or down regulated, such that expression, level, or activity is greater than or less than that observed in the absence of the modulator.

For example, the term "modulate" can mean "inhibit," but the use of the word "modulate" is not limited to this definition.

The terms "inhibit," "down-regulate," "reduce," or "knockdown," as used herein, means that the expression of the target gene, or level of RNA molecules or equivalent RNA molecules encoding one or more target proteins or protein subunits, or activity of one or more target proteins or protein subunits, is reduced below that observed in the absence of the polyribonucleotide molecules (e.g., siRNA) of the invention. In an embodiment, inhibition, down-regulation or reduction with a siRNA molecule is below that level observed in the presence of an inactive or attenuated molecule. In another embodiment, inhibition, down-regulation, or reduction with siRNA molecules is below that level observed in the presence of, for example, a siRNA molecule with scrambled sequence or with mismatches. In another embodiment, inhibition, down-regulation, or reduction of target gene expression with a nucleic acid molecule of the instant invention is greater in the presence of the nucleic acid molecule than in its absence.

In accordance with an embodiment of the present invention, the amount of time of exposure of the nanoplex molecules to the host cells, population of cells or subject should be sufficiently long to effect gene "knockdown" or modulation of the expression of the target gene in the host cell, population of cells or in the subject. The time for the desired effect varies with dosage, target, age and other factors known to those of skill in the art. Generally, the time of exposure of the nanoplex molecules to the host cells, population of cells or subject should range from about 1 hour to about 120 hours, preferably from about 1 hour to about 48 hours, more preferably from about 1 hour to about 24 hours.

By "target enzyme", is meant, a nucleic acid that encodes RNA, for example, nucleic acid sequences including, but not limited to, genes encoding a polypeptide which has enzymatic activity in the target cell. The target enzyme can be encoded by a gene derived from a cell, an endogenous gene, a transgene, or exogenous genes such as genes of a pathogen, for example a virus, which is present in the cell after infection thereof.

As used herein, the term "complementarity" or "complementary" means that a nucleic acid can form hydrogen bond(s) with another nucleic acid sequence by either traditional Watson-Crick or other non-traditional types. In reference to the polyribonucleotide molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, *CSH Symp. Quant. Biol.* LII pp. 123-133; Frier et al., 1986, *Proc. Nat. Acad. Sci. USA* 83:9373-9377; Turner et al., 1987, *J. Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively).

As used herein, the term "RNA" means a molecule comprising at least one ribonucleotide residue. By "ribonucleotide" is meant a nucleotide with a hydroxyl group at the 2' position of a β-D-ribo-furanose moiety. The terms "RNA," "ribonucleotides" and "polyribonucleotide," also include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA, or internally, for example, at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

In a further embodiment, the present invention provides one or more nanoplex molecules wherein the enzyme inhibitor portion comprises a double stranded RNA molecule or siRNA. The length of the siRNA molecule can be any length greater than about 10 bp, which is capable of binding its complementary sequence on the mRNA of the target gene of interest in the cytosol of a cell or population of cells. The length of the siRNA can be about 20 to about 50 bp, including, for example, 20 bp, 25 bp, 30 bp, 35 bp, 40 bp, 45 bp, up to and including 50 bp.

It is contemplated that any of the nanoplex molecule embodiments of the present invention described above can also encompass a pharmaceutical composition comprising the nanoplex molecules and a pharmaceutically acceptable carrier.

With respect to nanoplex molecules described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

The choice of carrier will be determined, in part, by the particular nanoplex molecule, as well as by the particular method used to administer the composition. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

As used herein the term "pharmaceutically active compound" or "therapeutically active compound" means a compound useful for the treatment or modulation of a disease or condition in a subject suffering therefrom. Examples of pharmaceutically active compounds can include any drugs known in the art for treatment of disease indications. A particular example of a pharmaceutically active compound is a chemotherapeutic agent.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

For purposes of the invention, the amount or dose of the nanoplex molecules of the present invention that is administered should be sufficient to effectively target the cell, or population of cells in vivo, such that the modulation of the expression of the target enzyme of interest, as well as the cytotoxicity of the nanoplex molecules can be detected, in the subject over a reasonable time frame. The dose will be determined by the efficacy of the particular nanoparticle formulation and the location of the target population of cells in the subject, as well as the body weight of the subject to be treated.

The dose of the nanoplex molecules of the present invention also will be determined by the existence, nature and extent of any adverse side effects that might accompany the administration of a particular nanoparticle. Typically, an attending physician will decide the dosage of the nanoplex molecules with which to treat each individual subject, taking into consideration a variety of factors, such as age, body weight, general health, diet, sex, compound to be administered, route of administration, and the severity of the condition being treated. By way of example, and not intending to limit the invention, the dose of the nanoplex molecules of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the nanoplex molecules of the present invention can be at a concentration from about 1 nM to about 10,000 nM, preferably from about 10 nM to about 5,000 nM, more preferably from about 100 nM to about 500 nM.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

The invention further provides a host cell comprising any of the nanoplex molecules described herein. As used herein, the term "host cell" refers to any type of cell that can contain the inventive nanoparticles. The host cell can be a eukaryotic cell, e.g., plant, animal, fungi, or algae. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, HeLa cells (human epithelial cervical cancer cell line), D407 cells (human retinal pigmented epithelial cell line), Chinese hamster ovarian cells, monkey VERO cells, COS cells, HEK293 cells, PC-3-PIP cells, and the like. For purposes of modulating the expression of a target gene of interest in a cell, the host cell is preferably a mammalian cell. Most preferably, the host cell is a human cell. Examples of suitable human host cells can include, but are not limited to, cells of the major organs of the body, including, for example, cells of the lung, including hepatocytes and hepatic stellate cells, cells of the breast, cells of the prostate, cells of the cornea, including corneal epithelial cells, cells of the lung, including lung epithelial cells, and cells of the brain, such as neurons. While the host cell can be of any cell type, can originate from any type of tissue, and can be of any developmental stage, the host cell preferably is a cancer cell, specifically a prostate cancer cell.

The population of cells can be a heterogeneous population comprising the host cell comprising any of the nanoplex molecules described, in addition to at least one other cell, e.g., a host cell (e.g., a epithelial cell), which does not comprise any of the nanoparticles, or a cell other than a epithelial cell, e.g., a macrophage, a neutrophil, an erythrocyte, a hepatocyte, a hepatic stellate cell, an endothelial cell, an epithelial cell, a muscle cell, a brain cell, etc. Alternatively, the population of cells can be a substantially homogeneous population, in which the population comprises mainly of host cells (e.g., consisting essentially of) comprising the nanoplex molecules.

In accordance with an embodiment of the present invention, the medicament for treating a disease in a subject can encompass many different formulations known in the pharmaceutical arts, including, for example, intravenous and sustained release formulations. With respect to the inventive methods, the disease can include cancer. Cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. Preferably, the cancer prostate cancer.

With various targeting portions, the nanoplex molecules of the present invention are useful in preparation of a medicament for treating other cancers. On of ordinary skill can determine which targeting molecules should be used for the various cancer indications, from the art.

As defined herein, in one or more embodiments, "administering" means that the one or more nanoplex molecules of the present invention are introduced into a sample having at least one cell, or population of cells, having a target gene of interest, and appropriate enzymes or reagents, in a test tube, flask, tissue culture, chip, array, plate, microplate, capillary, or the like, and incubated at a temperature and time sufficient to permit uptake of the at least one nanoplex molecules of the present invention into the cytosol, where it will bind to the mRNA of the target enzyme of interest and attenuate the expression of the target enzyme in the at least one cell or population of cells, while also providing bCD to the cell which will convert 5-FC to 5-FU when 5-FC is administered to the cell.

In another embodiment, the term "administering" means that at least one or more nanoplex molecules of the present invention are introduced into a subject, preferably a subject receiving treatment for a disease, and the at least one or more nanoplex molecules are allowed to come in contact with the one or more disease related cells or population of cells having the target gene of interest in vivo.

As used herein, the term "treat," as well as words stemming therefrom, includes diagnostic and preventative as well as disorder remitative treatment.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In a further embodiment, the nanoplex molecules of the present invention can be used in combination with one or more additional therapeutically active agents which are known to be capable of treating conditions or diseases discussed above. For example, the described nanoparticles of the present invention could be used in combination with one or more known therapeutically active agents, to treat a disease or condition. Non-limiting examples of other therapeutically active agents that can be readily combined in a pharmaceutical composition with the nanoplex molecules of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

EXAMPLES

Figure 1B:
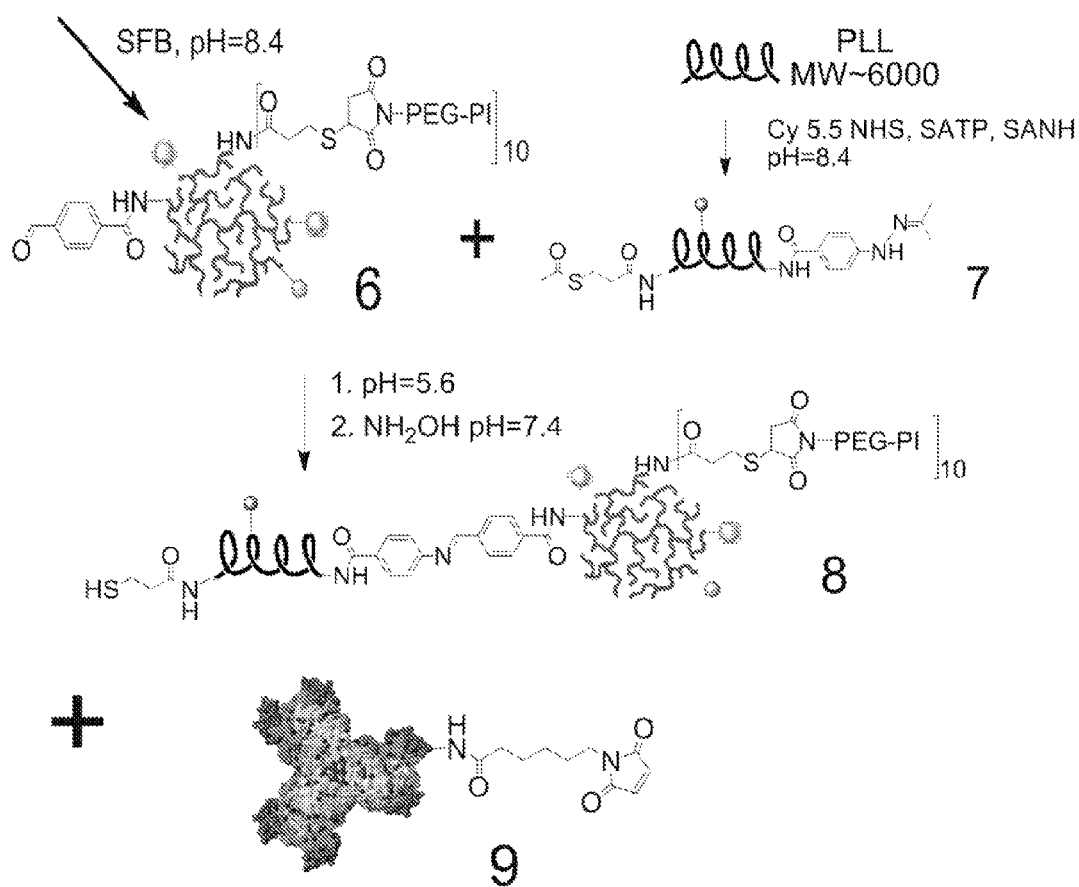
Figure 1C:
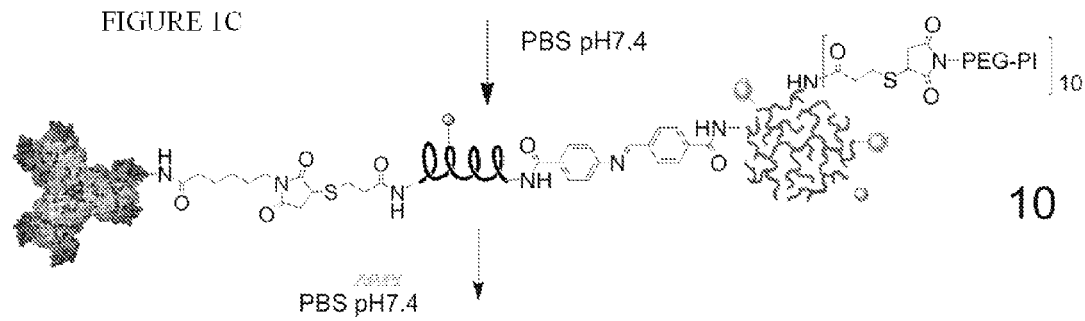
Figure 2:
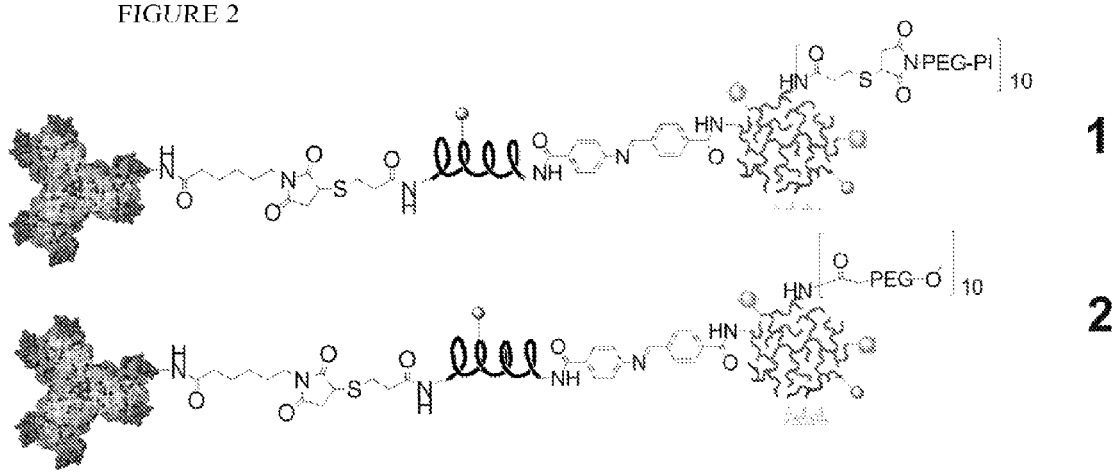
FIG. 2 shows a schematic representation of the structure of nanoplex 1 designed with the PSMA targeting moiety, and of nanoplex 2 that does not contain the PSMA targeting moiety.

Synthesis. The bCD was produced as previously described by us (23, 24). A brief synthesis route of the nanoplex is outlined in FIG. 1. Initially, a N-hydroxysuccinamide (NHS) ester of the low molecular weight urea-based PSMA binder/inhibitor (PI) (2-(3-[1-carboxy-5-[7-(2,5-dioxo-pyrrolidin-1-yloxycarbonyl)-heptanoylamino]-pentyl]-ureido)-pentanedioic acid; Mw 572.56), i.e, a functionalized targeting moiety, was generated. PI-NHS was conjugated with maleimide-PEG-NH2 (3.4 kDa; Company (Nanocs. Inc., NY) to form PI-PEG-maleimide. N-succinimidyl-5-acetylthiopropionate (SATP) (Pierce, Rockford, Ill.) was conjugated to PEI (Sigma Milwaukee, Wis.) (25 kDa) at a 10:1 molar ratio of SATP:PEI and then the SATP moiety was reduced to form a free sulfydryl group. Reaction between this sulfydryl and PI-PEG-maleimide generated PI-PEG-PEI (compound 3). Compound 3 was labeled with NHS-rhodamine (Sigma Milwaukee, Wis.) and NHS-DOTA using previously described in-house synthesis (25) to form compound 4. Compound 4 was reacted with $^{111}InCl_3$ in sodium acetate buffer (pH=~4.6-5.5) to form $^{111}In$-labeled PEI (compound 5). That radioactive compound was conjugated with succinimidyl 4-formylbenzoate (SFB) (Pierce, Rockford, Ill.) in HEPES buffer at pH 8.4 to form compound 6. PLL (poly-L-lysine) (Sigma Milwaukee, Wis.) (~20 kDa) was labeled with Cy5.5-NHS (GE Healthcare, Piscataway, N.J.), SATP and succinimidyl 6-hydrazinonicotinamide acetone hydrazine (SANH) (Pierce, Rockford, Ill.) to produce compound 7. Conjugation of 6 and 7 at pH 7.4 produced the PEI-PLL copolymer, which was reduced to form compound 8 that contained a free sulfydryl group. Treatment of bCD with N-[e-Maleimidocaproyloxy)-succinimideester (EMCS) (Pierce, Rockford, Ill.) produced 9. Equimolar amounts of 9 and 8 were crosslinked through the reaction of maleimide and sulfydryl to provide the bCD-PLL-PEI, (compound 10). Finally, binding of siRNA with 10 gave the PSMA-targeting bCD-PLL-PEI/siRNA nanoplex termed nanoplex 1. We also synthesized nanoplex 2, which was identical to nanoplex 1, but without the PSMA-targeting moiety as a non-targeted control reagent. The final structures of nanoplex 1 and 2 are shown in FIG. 2.

During synthesis, the amounts of PEI, and PLL were measured through the absorption coefficients of rhodamine (attached on PEI), Cy5.5 (attached on PLL), and bCD at 279 nm as previously described (*ACS Nano.*, 2010 4:6707-16). The final molar ratio of PEI:PLL:bCD was: 1:1.1:1.1. Size-exclusion chromatography was used to determine the molecular weight of 375 kDa of the nanoplex. The longitudinal size and zeta-potential of the nanoplex were 65 nm and 1.6 mV, respectively, as measured by dynamic light scattering (DLS). Cytosine and 5-FC were used as substrates to evaluate the activity of the prodrug enzyme. The kinetic constants were determined by monitoring changes in the absorbance of cytosine versus 5-FC at saturating substrate concentrations, as reported previously by us (Id.). Nanoplex 1 was found to have Km values similar to those found for native bCD for both substrates. Those results indicated that conjugation of bCD to PEI-PLL did not hamper the function of bCD. Electrophoretic gel mobility shift assay indicated that nanoplex 1 retained strong binding with siRNA at an N/P ratio of 50.

siRNA. The siRNA-Chk duplex directed against human Chk mRNA (sense: 5'-CAUGCUGUUCCAGUGCUCCUU-3' (SEQ ID NO: 1) and antisense: 5'-GGAGCACUG-GAACAGCAUGUU-3' (SEQ ID NO: 2)) and the scrambled siRNA were purchased from Dharmacon (Lafayette, Colo.) and designed using their ON-TARGET plus program.

Cell culture. Human PC PC3 cells transfected to overexpress PSMA (PC3-PIP) or transfected with the plasmid alone (PC3-Flu) were obtained from Dr. Warren Heston (Cleveland Clinic, Cleveland, Ohio). Cells were maintained in RPMI 1640 (Invitrogen, Grand Island, N.Y.) supplemented with 10% fetal bovine serum in a humidified incubator at 37° C./5% $CO_2$.

In vitro cell culture studies. The cytotoxicity of the nanoplex was evaluated by an MTT (3-(4,5-Dimethylthiazol-2-yl)-2,5-diphenyltetrazolium bromide) assay (Sigma, Milwaukee, Wis.). PC3-PIP cells ($2 \times 10^3$ cells/well) in 96-well plates were incubated for 24 hours in RPMI 1640 prior to treatment. To evaluate the therapeutic efficacy induced by down-regulation of Chk, the cells were treated with nanoplex 1 (N/P=50, 80 nM siRNA/350 nM nanoplex 1). To test the therapeutic efficacy of the prodrug strategy, the cells were treated with nanoplex 1 (350 nM) without siRNA with the addition of 5-FC (3 mM). To evaluate the combined therapeutic efficacy of siRNA and prodrug strategy, cells were treated with nanoplex 1 (N/P=50, 80 nM siRNA/350 nM nanoplex 1) with the addition of 5-FC (3 mM).

Confocal laser scanning fluorescence microscopy. The cells were treated with either nanoplex 1 or 2 at different concentrations for 2 hours, then washed 3 times with PBS buffer at pH 7.4. An ethanol/acetic acid/formaldehyde (85/5/10) solution was used to fix the treated cells, following which cell nuclei were stained with DAPI (4',6-diamidino-2-phenylindole) for 5 minutes. Fluorescence microscopic images of PC3-PIP and PC3-Flu cells were generated on a Zeiss LSM 510 META confocal laser scanning microscope (Carl Zeiss, Inc. Oberkochen, Germany). Rhodamine and DAPI fluorescence images were obtained using $\lambda ex=543$ nm and $\lambda em=560$ nm, and $\lambda ex=405$ and $\lambda em=420-480$ nm filter sets respectively.

Immunoblot analysis of PC3-PIP cells. PC3-PIP cells were treated with different concentrations of the nanoplex for 24 hours, following which cells were collected after washing 3 times with cold PBS buffer. Proteins were extracted using RIPA buffer with protease inhibitor cocktail (1/500, Sigma, St. Louis, Mo.), dithiothreitol (1/1,000, 1M stock), phenylmethylsulfonyl fluoride (1/200, 0.2M stock), sodium orthovanadate (1/500, 0.5M stock) and sodium fluoride (1/500, 0.5M stock). About 100 μg of protein was resolved on 10% SDS-PAGE, transferred onto nitrocellulose membranes, and probed with a mouse monoclonal antibody against PSMA (Abcam, Cambridge, Mass., USA) or with a custom-made polyclonal antibody against Chk (Proteintech Group, Inc., Chicago, Ill.) as previously described (*Cancer Res.*, 2005 65:11034-43). Appropriate horseradish peroxidase (HRP) conjugated secondary antibody donkey anti-mouse antibody was used at 1/2,000 dilution. A mouse monoclonal antibody against GAPDH (Sigma, St. Louis, Mo.) at 1/1,000 was used as loading control Immunoblots were developed using SuperSignal West Pico chemiluminescent substrate kit (Pierce Biotechnology, Inc., Rockford, Ill.). Intratumoral Chk levels in cells before and after treatment were visually evaluated by immunoblot analyses.

Mouse model and tumor implantation. All in vivo studies were done in compliance with guidelines established by the Institutional Animal Care and Use Committee of The Johns Hopkins University. PC3-PIP and PC3-Flu human PCa cells ($2 \times 10^6$ cells/mouse) were inoculated subcutaneously in severe combined immunodeficient (SCID) male mice. Tumors were palpable within one week after implantation and reached a volume of approximately 300 to 400 mm³ within three weeks, at which time they were used for experiments Immunogenicity and toxicity studies were performed in immunocompetent Balb/C mice.

SPECT/CT Imaging. SPECT imaging of SCID mice bearing PC3-PIP and PC3-Flu tumors was performed with [$^{111}$In]DOTA-radiolabeled nanoplex 1 (770±208 μCi, 150 mg/kg dose injected intravenously in 0.2 ml of PBS, n=4). A dedicated small-animal SPECT/CT system (Gamma Medica X-SPECT, Northridge, Calif.) was used for image acquisition. SPECT/CT images were obtained at 48 hours post-injection with an energy window of 170-250 keV. Tomographic data were acquired in 64 projections over 360 degrees at 40 s/projection. Following SPECT, CT images were acquired with 512 projections. Data were reconstructed using an ordered subsets-expectation maximization (OS-EM) algorithm and analyzed using AMIDE software (SourceForge; sourceforge.net/projects/amide/). To calculate the amount of accumulated radioactivity, images were normalized to the injected dose and regions of interest were drawn over the whole tumor.

In vivo MRS. PC3-PIP tumor bearing mice were anesthetized with a mixture of ketamine (25 mg/kg) and acepromazine (2.5 mg/kg) injected i.p. before all MR studies. Anesthetized mice were imaged on a 9.4 T Bruker Biospec spectrometer (Bruker Biospin Co., Billerica, Mass.) using a solenoid coil placed around the tumors. Body temperature of the animals in the magnet was maintained by a thermostat-regulated heating pad.

In vivo $^1$H MRS. MRSI was performed using a two-dimensional (2D) chemical shift imaging (CSI) sequence. A reference image from a 4 mm thick central slice of the tumor was acquired using a spin-echo sequence. Water-suppressed MRSI was performed on the same 4 mm thick central slice, with an in-plane resolution of 1 mm×1 mm per pixel using a 2D CSI sequence with VAPOR water suppression and the following parameters: echo time (TE) of 120 ms, repetition time (TR) of 1000 ms, field of view of 1.6 cm×1.6 cm, phase encode steps of 16 (16×16 matrix), number of scans (NS) 4, block size 512, and sweep width of 7,000 Hz. Water MR spectroscopic images were also acquired without water suppression on the same slice, with TE=20 ms and NS=1, and with all other parameters remaining the same. Spectroscopic images of the total choline containing compound (tCho) signal at 3.2 ppm and the water signal at 4.7 ppm were generated from the MRSI data sets using an in-house IDL program. These images were imported in the freeware NIH program ImageJ (rsbweb.nih.gov/ij/) for analyses.

In vivo $^{19}$F MRS. All $^{19}$F MRS experiments were done using a solenoid coil tunable to $^{1}$H or $^{19}$F frequency. Typically, after injection of 5-FC (450 mg/kg), anesthetized mice (n=3) were placed on a plastic cradle to allow positioning of the tumor in the RF coil. Following shimming on the water proton signal, serial $^{19}$F nuclear MR spectra were acquired from the tumor every 30 minutes for 110 minutes using a one-pulse sequence (flip angle, 60°; repetition time, 0.8 s; number of average, 2000; spectral width, 10 kHz). $^{19}$F MR spectra were processed with an in-house XsOs nuclear magnetic resonance software developed by Dr. D. Shungu (Cornell University, New York, N.Y.). The chemical shift of the 5-FU resonance was set to 0 ppm.

Blocking experiments and ex vivo optical imaging studies. For the binding specificity (blocking) studies, 100 μg of anti-PSMA mouse monoclonal antibody (Clone GCP-05, Abcam, Cambridge, Mass.) were injected i.v. in a volume of 0.05 ml PBS in PC3-PIP and PC3-Flu tumor bearing mice. Five hours after injection of antibody, 1.5 mg of nanoplex 1 (75 mg/kg) were injected i.v. in the same mice. Mice were sacrificed 48 hours after nanoplex injection. Tumors, muscle and kidney were excised and optical images were obtained on the IVIS Caliper Spectrum optical scanner (Caliper Life Sciences, Hopkinton, Mass.). A Cy5.5 excitation (615-665 nm) and emission (695-770 nm) filter set was used to acquire the Cy5.5 fluorescence data. Cy5.5 fluorescence images were acquired using a λex=615-665 nm and λem=695-770 nm filter set, 1 s exposure time, and the fluorescence intensity was scaled as units of $ps^{-1} cm^{-2} sr^{-1}$.

Blood analysis. All blood analyses were performed by the Johns Hopkins Phenotyping and Pathology Core. Alanine aminotransferase (ALT), aspartate aminotransferase (AST), creatinine and blood urea nitrogen measurements were done on mouse serum 48 hours post-injection of 150 mg/kg nanoplex 1. For the immunogenicity studies, blood cell counts were performed on heparinized blood samples from immunocompetent Balb/C mice that were injected i.v. with 150 mg/kg nanoplex 1 every 3 days for a total of three injection. An additional comparison was made with immunocompetent mice injected with Feridex (Advanced Magnetics Inc., Cambridge, Mass.) injected at a dose of 10 mg/kg of Feridex, which is in the range of typical concentrations used in preclinical studies, with the same injection schedule as for the nanoplex.

Example 1

Cellular characterization of nanoplex 1. To evaluate the specificity of nanoplex 1 to PSMA, laser fluorescent confocal microscope imaging was applied to investigate the uptake of nanoplex 1 and 2 in PC3-Flu (PSMA negative) and PC3-PIP (PSMA positive) cells (data not shown). After 2 hours of incubation, the uptake of 5 nM nanoplex 1 in PC3-PIP was high whereas the uptake of 5 nM of nanoplex 2 in PC3-PIP was much lower. When excess PMPA (2-phosphonomethylpentanedioicacid) was added to block PSMA, the uptake of nanoplex 1 in PC3-PIP cells decreased to levels similar to the uptake of nanoplex 2. When nanoplex 1 or 2 was added to PC3-Flu cells that have low PSMA expression, the uptake was low. When the concentration was reduced to 0.5 nM, fluorescence was only observed when PC3-PIP cells were treated with nanoplex 1, which has PSMA-specific binding.

Figure 3A:
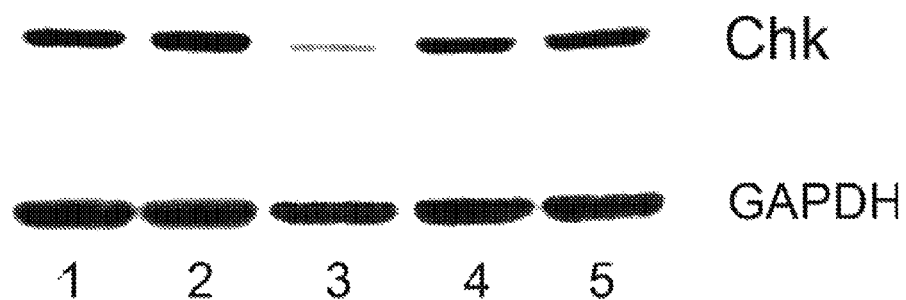
FIG. 3A shows a representative immunoblot showing that in PC3-PIP cells the down-regulation of Chk following 24 hours of incubation with nanoplex 1 was dependent on the concentration of siRNA-Chk incorporated into the nanoplex (N/P ratio is 50). GAPDH protein levels were used for protein loading assessment. Lane 1: PC3-PIP cells treated with nanoplex 1 without siRNA-Chk; Lane 2: PC3-PIP cells treated with nanoplex 1 with 100 nM scrambled siRNA; Lane 3: PC3-PIP cells treated with nanoplex 1 with 100 nM siRNAChk; Lane 4: PC3-PIP cells treated with nanoplex 1 with 50 nM siRNA-Chk; and Lane 5: PC3-PIP cells treated with nanoplex 1 with 20 nM siRNA-Chk.

The MTT assay demonstrated that nanoplex 1 had almost no effect on cell viability at concentrations lower than 2 μM. The transient transfection delivery efficiency of siRNA with nanoplex 1 into PC3-PIP cells was evaluated with immunoblotting. As shown in FIG. 3A, down-regulation of Chk by the nanoplex 1-siRNA complex was dependent on the concentration of siRNA used. After 24 hours of incubation, a concentration of 100 nM siRNA-Chk (lane 3) showed the largest down-regulation of Chk protein, to nearly undetectable levels, relative to 50 or 20 ng (lane 4 and 5 respectively). The latter two treatments show Chk protein levels remained similar to those seen without siRNA or with scrambled siRNA treatments (lane 1 and 2 respectively).

Figure 3B:
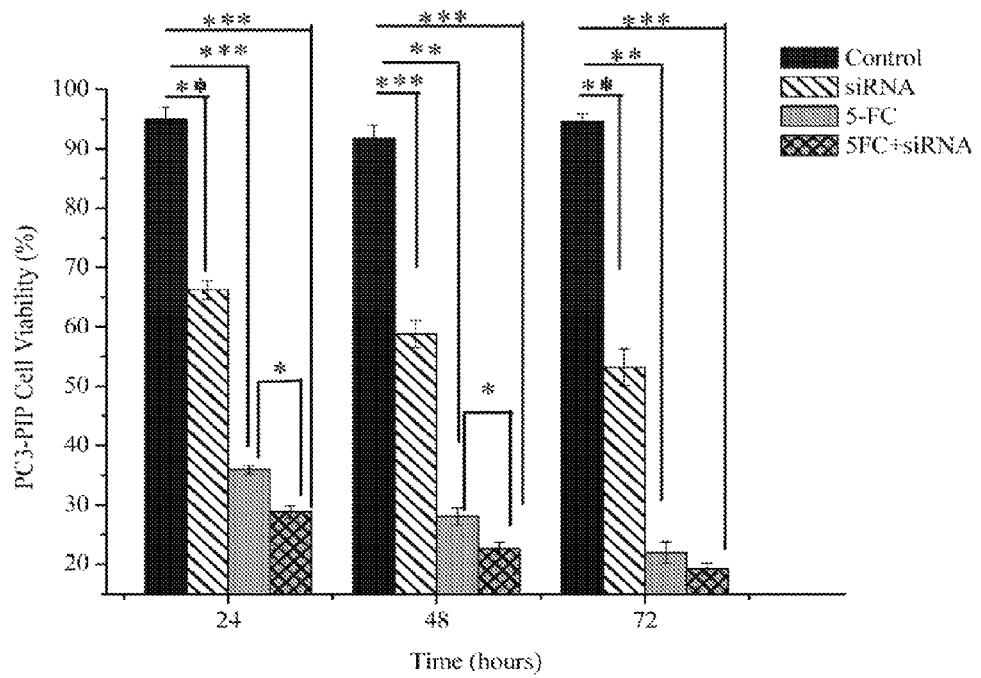
FIG. 3B depicts the therapeutic efficacy of siRNA and prodrug in PC3-PIP cells. PC3-PIP cells were treated with nanoplex 1 without siRNA-Chk (control), nanoplex 1 with siRNA-Chk (siRNA-Chk), nanoplex 1 without siRNA-Chk but with 5-FC (5-FC), and nanoplex 1 with siRNA-Chk and 5-FC for 24, 48 and 72 hours (siRNA-Chk+5-FC). (1. Treatment for 24 hours; 2. Treatment for 48 hours; 3. Treatment for 72 hours; Nanoplex concentration=350 nM, N/P=50, siRNA-Chk concentration=80 nM, 5-FC concentration=3 mM). Values represent Mean±SEM of three or more assays for each treatment; *, $P<0.05$; , $P<0.01$; *, $P<0.001$.

The therapeutic efficacy of siRNA, prodrug, and combination therapy in PC3-PIP cells is presented in FIG. 3B. With nanoplex 1 (350 nM) alone, cell viability remained above 95% throughout the 72 hour incubation period. With siRNA-Chk bound to nanoplex 1 (350 nM nanoplex, 80 nM siRNA, N/P=50), cell viability decreased about 65% after 24 hours and to less-than 60% after 48 and 72 hours of incubation. When cells were incubated with 350 nM of nanoplex 1 with 3 mM 5-FC but without siRNA for 1-3 days, cell viability was reduced to about 40% after 24 hours, 25-30% after 48 hours, and near 20% at 72 hours. Finally, when cells were incubated with 350 nM nanoplex 1 complexed with 80 nM siRNA plus 3 mM 5-FC, the decrease in cell viability after 24 hours was 30%, which was significantly lower than either therapy used alone at this time point. This trend was also observed at 48 hours but by the 72 hour time point there was no significant difference in viability between treatment with 5-FC alone and the combined treatment. This was most likely due to a combination of decreasing cell viability due to the longer exposure of cells to 5-FU, and the weakening of siRNA downregulation of Chk by 72 hours, resulting in a convergence of cell viability values for cells treated with 5-FC alone and cells treated with siRNA and 5-FC.

Example 2

Figure 4A:
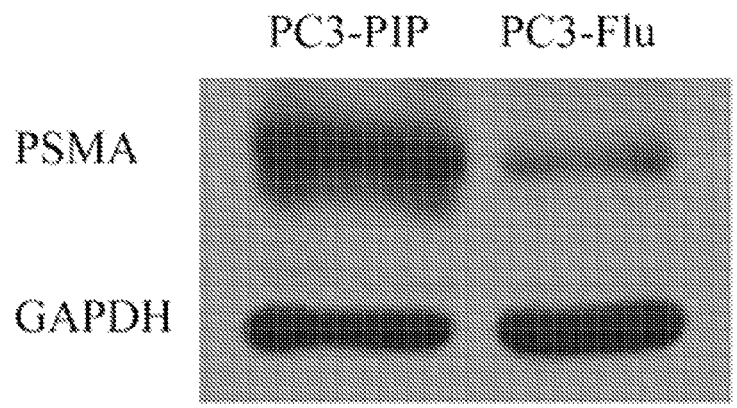
FIG. 4A is a representative immunoblot showing PSMA protein expression in PC3-PIP and PC3-Flu cells. GAPDH was used as a loading control.
Figure 4B:
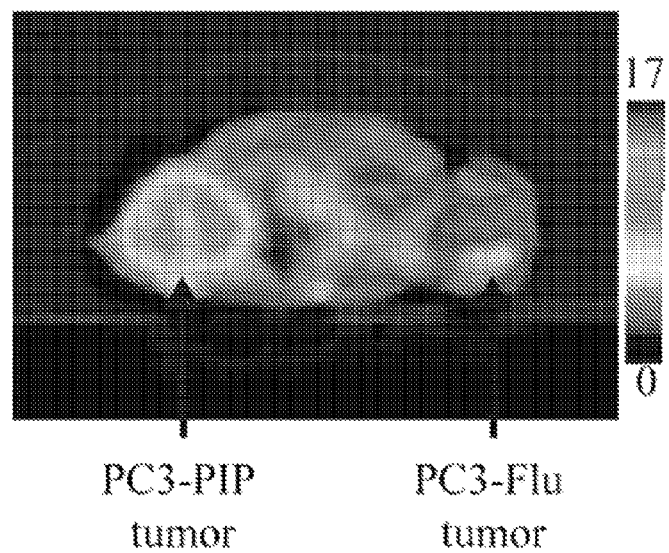
FIG. 4B shows representative SPECT images of a SCID mouse bearing PC3-PIP and PC3-Flu tumors. Mice were injected i.v. with 776 μCi of 111In labeled PSMA targeted nanoplex 1 (150 mg/kg in 0.2 ml of PBS). SPECT images were acquired in 64 projections at 30 s/projection. Following tomography, CT images were acquired in 512 projections to allow co-registration. Decay corrected transaxial SPECT imaging slice (slice thickness 5 mm) of a representative mouse showed clear accumulation of radioactivity in PC3-PIP tumor at 48 hours.
Figure 4C:
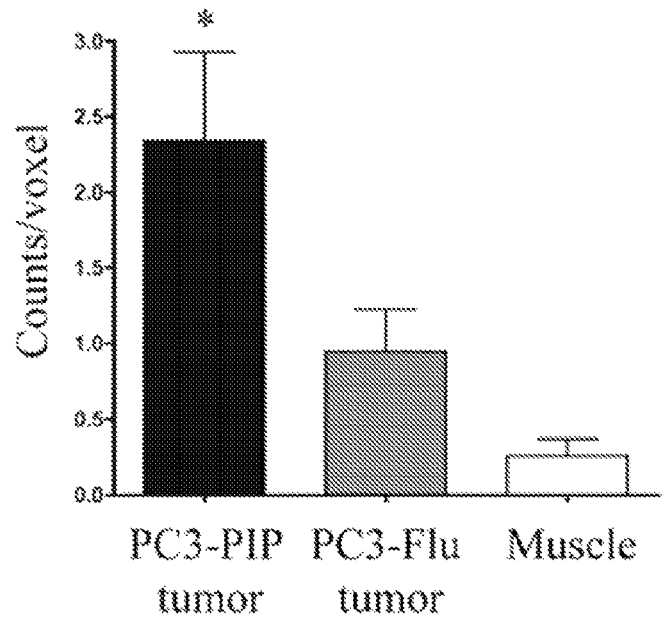
FIG. 4C depicts the ROI analysis of tumors and muscle showed significant accumulation of activity in PC3-PIP tumors at 48 hours post injection. Values represent Mean±SEM (n=4, *, P<0.05 with PC3-Flu tumor uptake as the comparative reference).
Figure 4D:
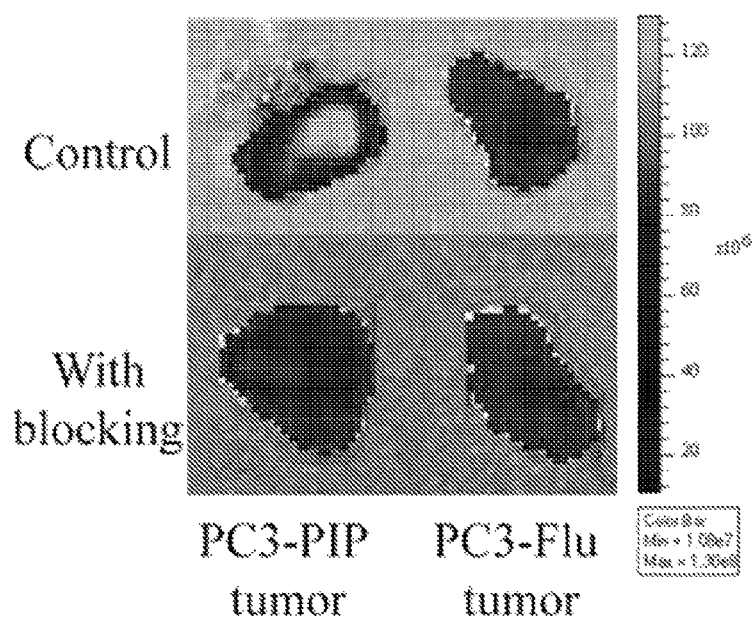
FIG. 4D shows the nanoplex molecule accumulation in PC3-PIP and PC3-Flu tumors without and with blocking. Representative tumors excised at 48 hours after nanoplex injections are shown. Images were acquired on the Caliper Spectrum scanner to detect Cy5.5 signal. For the blocking studies 100 µg of anti-PSMA antibody was injected i.v. in PC3-PIP and PC3-Flu tumor bearing mice. Five hours after injection of antibody, 75 mg/kg of nanoplex 1 was injected i.v. in the same mouse.

Higher specific uptake of the targeted nanoplex in PSMA overexpressing tumors. Immunoblot analysis of PC3-PIP and PC3-Flu cell extracts confirmed the differential expression of PSMA as shown in the representative immunoblot in FIG. 4A. SPECT/CT images obtained from mice bearing PC3-PIP and PC3-Flu tumors revealed a significantly higher uptake of the targeted nanoplex in PSMA-overexpressing PC3-PIP tumors compared to PC3-Flu tumors (FIGS. 4B and 4C). To confirm the specificity of this uptake, blocking experiments were performed by injecting antibody directed against PSMA 5 hours before injecting nanoplex 1. Optical imaging analysis performed on tissue slices without or with PSMA blocking in mice bearing PC3-PIP and PC3-Flu tumors demonstrated increased uptake in PC3-PIP tumors compared to PC3-Flu, which was reduced with blocking, confirming the in vivo results obtained by SPECT imaging (FIG. 4D).

Example 3

Figure 5A:
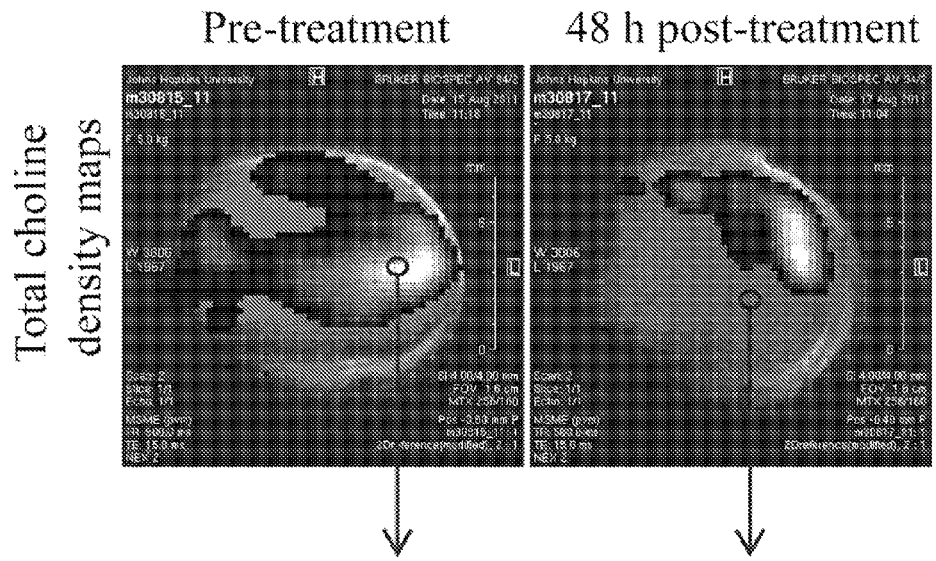
FIG. 5A depicss in vivo tCho density maps from 2D CSI data sets acquired from a representative PC3-PIP tumor (~400 mm3) before and 48 hours after i.v. injection of the PSMA-targeted nanoplex 1 (150 mg/kg). Parameters used were TE=120 ms, TR=1000 ms, 4 scans per phase encode step. CSI spectra were acquired at 9.4T with an in-plane spatial resolution of 1 mm×1 mm from a 4 mm-thick slice.
Figure 5C:
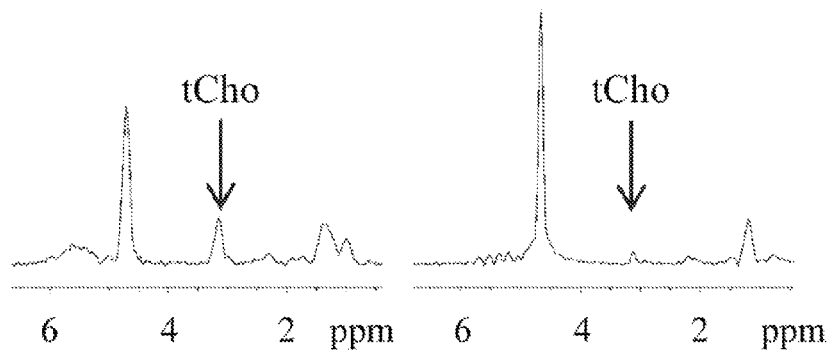
FIG. 5C is a representative one voxel spectra from 2D CSI represented in 5A and 5B.
Figure 5B:
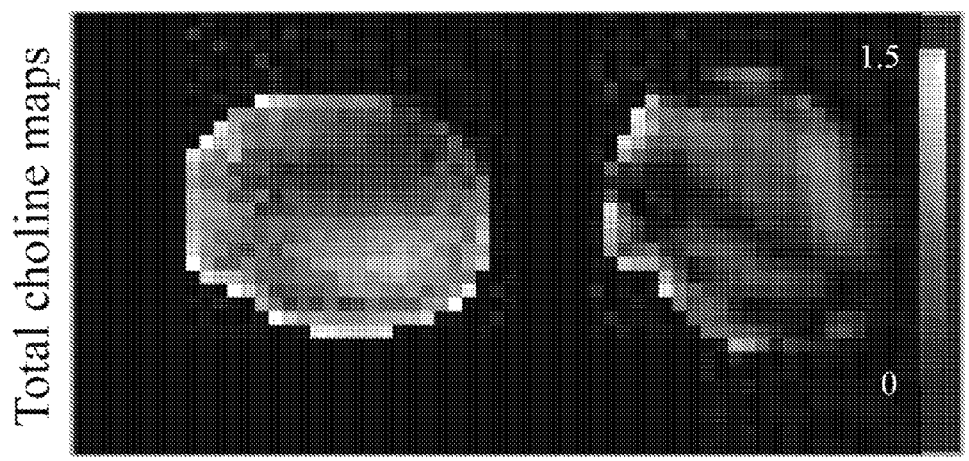
FIG. 5B shows corresponding in vivo tCho maps from the same 2D CSI data sets.
Figure 5D:
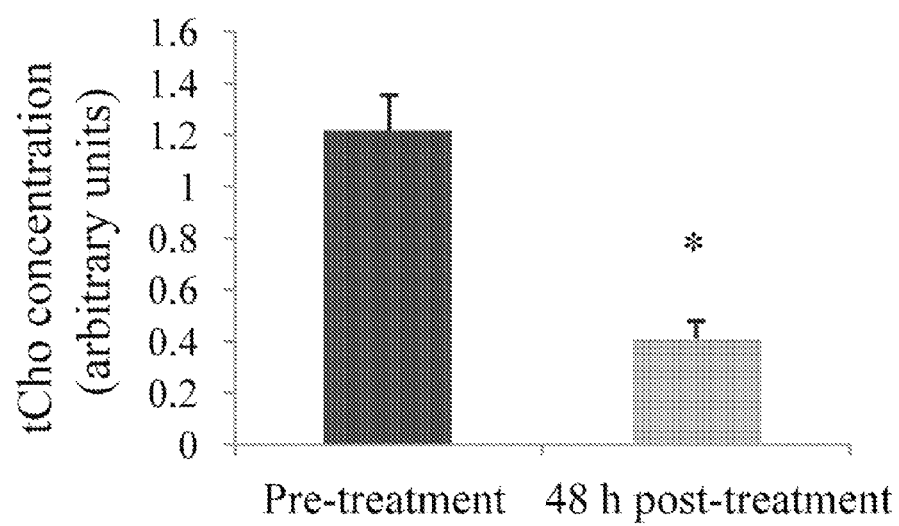
FIG. 5D provides that the tCho concentration calculated in arbitrary units before and at 48 hours after injection of nanoplex 1. Values represent Median±SEM (n=3 , *, P<0.05).
Figure 5E:
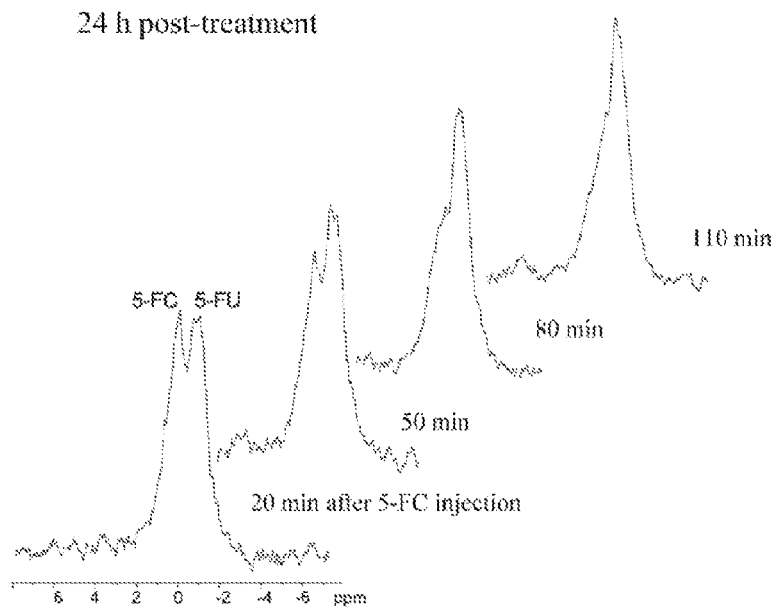
FIG. 5E shows in vivo $^{19}$F MR spectra acquired from a PC3-PIP tumor (~400 mm3) at 24 hours and 48 hours post i.v. injection of the PSMA-targeted nanoplex (150 mg/kg) carrying bCD and siRNA-Chk. Spectra were acquired after a combined i.v. and i.p. injection of 5-FC (450 mg/kg), on a Bruker Biospec 9.4 T spectrometer using a 1 cm solenoid coil tunable to $^1$H and $^{19}$F frequency. Following shimming on the water proton signal, serial nonselective $^{19}$F MR spectra were acquired starting 20 minutes after the 5-FC injection and continued every 30 minutes for 110 minutes with a repetition time of 0.8 s, a number of scans of 2,000, and a spectral width of 10 KHz.
Figure 5E:
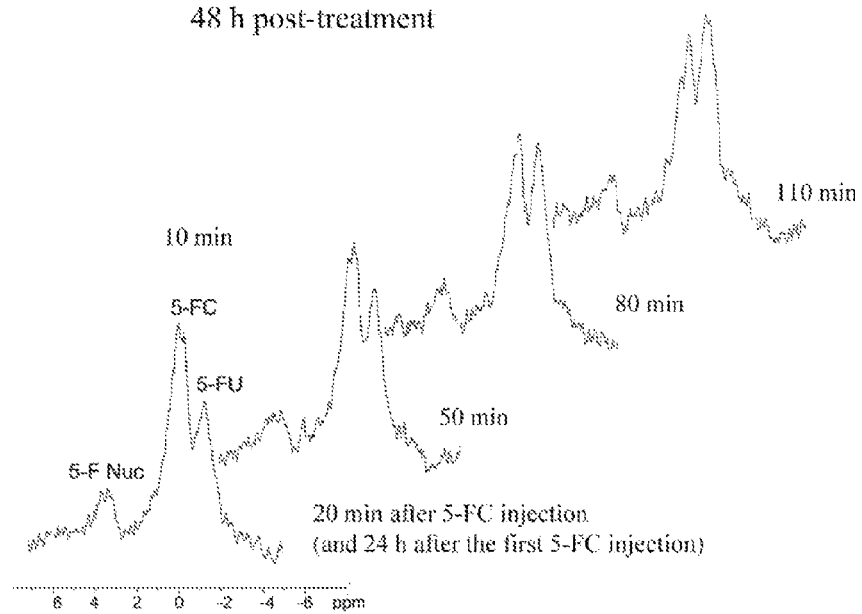

In vivo assessment of Chk inhibition and bCD activity. To assess the efficacy of siRNA-Chk to down-regulate Chk, we acquired in vivo $^{1}$H MRSI of PC3-PIP tumors 48 hours after administration of nanoplex 1. We observed a significant decrease of the tCho signal as shown in FIGS. 5A-5D. Prior to injection, tCho was detected throughout large portions of each tumor. However, tCho decreased significantly within 48 hours post-injection in the tumor and was largely localized to a thin rim at the tumor periphery. On average, tCho levels decreased to about 30% of pretreatment values at 48 hours post-injection. Moreover, by performing $^{19}$F MRS, we observed that the prodrug enzyme bCD was still active at 24 hours and 48 hours post-injection, as it continued to convert the prodrug 5-FC to 5-FU over this time (FIG. 5E).

Example 4

Figure 6A:
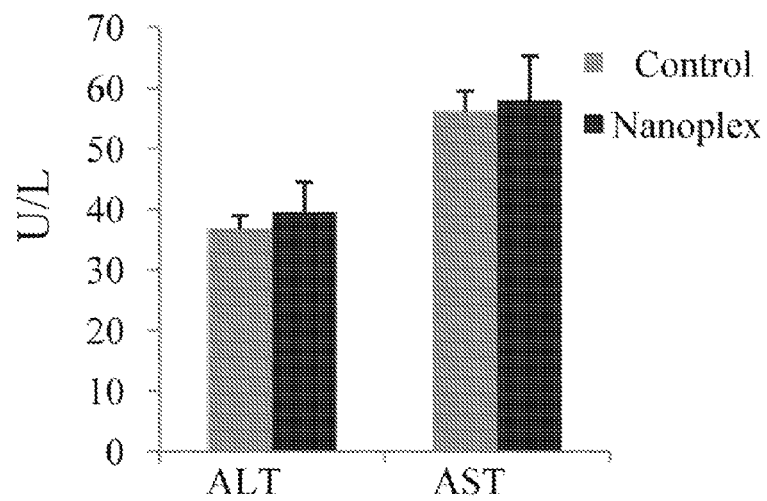
FIG. 6A shows alanine aminotransferase (ALT) and aspartate aminotransferase (AST) measurements at 48 hours post-injection of 150 mg/kg nanoplex 1 per mouse (n=4).
Figure 6B:
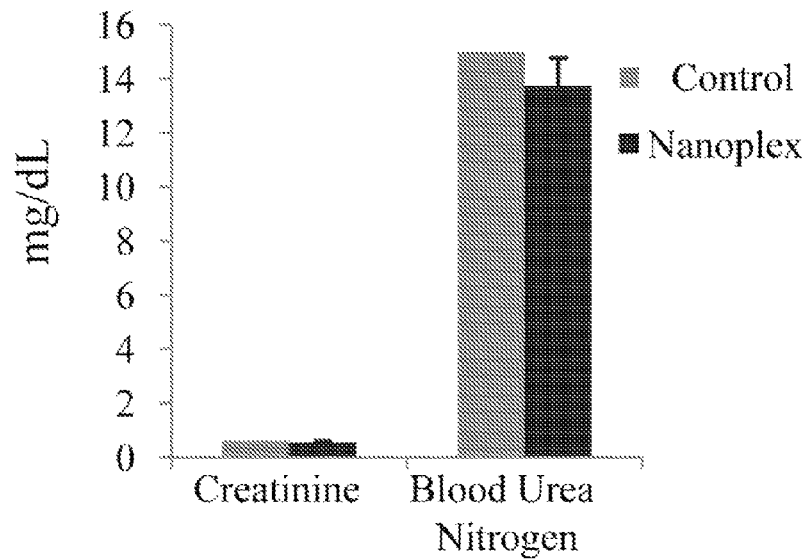
FIG. 6B provides creatinine and blood urea nitrogen measurements at 48 hours post-injection of 150 mg/kg nanoplex 1 per mouse (n=4).
Figure 6C:
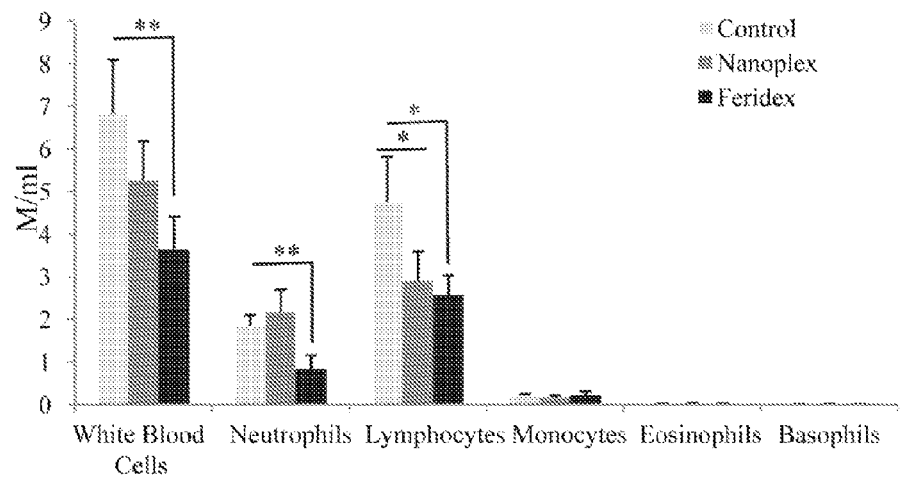
FIGS. 6C and 6D show results from the immunogenicity studies (150 mg/kg of nanoplex 1 injected every 3 days for a total of three injection). Values represent Mean±SEM (*, P<0.05; , P<0.01; *, P<0.001, n=4). (M/ml denotes million/ml).
Figure 6D:
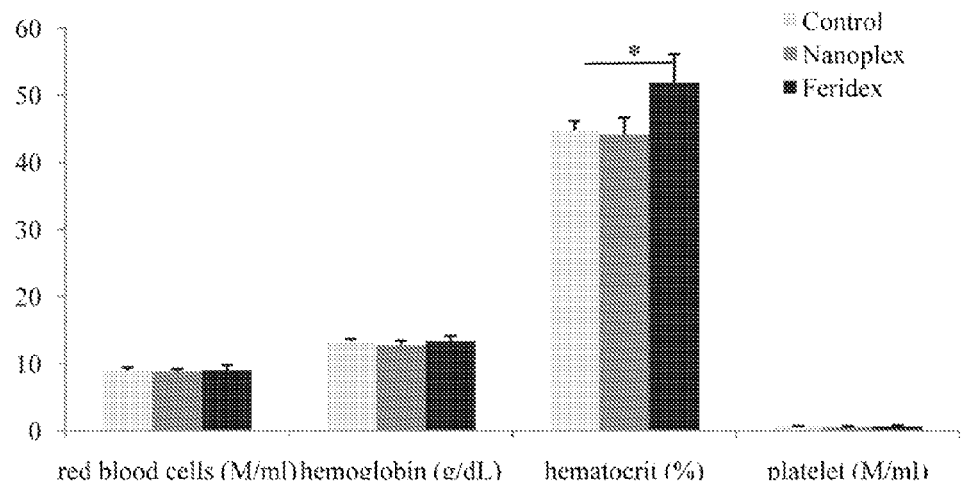

Assessment of toxicity and immunogenicity. ALT, AST, creatinine and blood urea nitrogen measurements were performed to assess the hepatic and renal toxicity of the nanoplex (FIGS. 6A-6B). No significant differences were observed in these four parameters between the treated group injected with nanoplex 1, and the control group injected with PBS. We also studied the immunogenicity of nanoplex 1 by measuring the white blood cell count after three repeated injections (FIG. 6C). Total white blood cell (WBC) counts did not increase after the injections. Instead we observed a decrease of WBCs. This was mainly because lymphocytes numbers decreased although the values remained within the normal range (0.9-9.3 Million/ml). Red blood cells and platelets were not affected by nanoplex injections (FIG. 6D). We compared the effects of nanoplex injections to those induced by similar injections of Feridex. At the dose used, Feridex was found to significantly decrease blood cell counts and increase hematocrit compared to nanoplex 1 (FIGS. 6C-6D).

Example 5

Although the nanoplex molecules of the present invention can, at relatively high concentrations, enter cells through endocytosis, the cellular and in vivo binding specificity studies demonstrated that the PSMA targeting moiety enhanced the uptake of the nanoplex in PSMA expressing cells and tumors. Increased retention of nanoplex 1 was observed in PSMA over-expressing tumors in vivo. Further evidence of specificity was provided by the blocking studies in which the differential retention was eliminated once PSMA was blocked with prior administration of anti-PSMA-antibodies.

The SPECT-CT imaging data detected an increased accumulation of nanoplex 1 in PC3-tumors at 48 hours after injection. The higher permeability of the tumor vasculature provided a natural selection process for allowing the nanoplex to leak out extensively in tumors but not in normal tissue. However, because of the specificity of the PSMA targeting moiety, the accumulation of nanoplex 1 was much higher in PC3-PIP than in PC3-Flu tumors. It is apparent from the SPECT images that there was significant accumulation of the nanoplex in the liver. In addition, mouse (but to a lesser extent human) kidneys express PSMA. However down-regulation of Chk, the siRNA target selected, does not affect non-malignant cells. In addition, the liver contains high levels of dihydropyrimidine dehydrogenase (DPD), which catabolizes 5-FU to dihydrofluorouracil (DHFU). This can explain the absence of hepatic or renal toxicity due to the nanoplex.

It was found that branched PEI can be used as an efficient siRNA delivery vector because of its buffering effect, which resulted in endosomal release of endocytosed siRNA into cytoplasm. There were approximately 10 PEG chains on the surface of one PEI molecule. The molar excess of PEG served as a bridge between the PSMA targeting moiety and the nanoplex, and also sterically shielded the relatively large net positive charge on the surface of the PEI, which might otherwise hinder the functioning of the PEI and nanoplex. Shielding of the positive charge reduces the toxicity of PEI in part through decreased interactions of the PEI with blood and cellular components. Conjugation of the PEI of the nanoplex with hydrophilic PEG increased the $IC_{50}$ to about 30 times that of the nanoplex without PEG modification.

The prodrug enzyme bCD displayed high stability and, importantly, it was possible to detect enzyme activity noninvasively with $^{19}$F MRS. The present invention demonstrates that bCD maintains high activity even after conjugation with PEI. In an embodiment, PLL was chosed as the linker between the PEI and bCD to minimize interactions between PEI and bCD, and thus maintain bCD activity. The bCD enzyme attached to the nanoplex was active up to 48 hours post-injection and was able to convert the non-toxic prodrug 5-FC into the toxic 5-FU efficiently throughout the time course of these experiments.

The siRNA of the present invention, directed against Chk, induced a decrease in the tCho signal, which was visible in vivo with $^1$H MRSI. Proton and $^{19}$F MRS techniques are noninvasive and are easily translated to the clinic. Here the present invention shows that it is possible to assess noninvasively the conversion of 5-FC into 5-FU in the tumor, along with the efficacy of down-regulating Chk by acquiring $^{19}$F spectra and tCho maps with $^1$H MRSI, respectively.

To achieve systemic therapy safely, it is important to have control over where the toxic species are delivered—preferentially within tumor, leaving normal tissues unharmed. This control is achieved through the nanoplex molecules of the present invention, and being able to measure the delivery of that nanoplex through imaging. There is also a compelling need to find effective treatments for metastatic disease, as it typically becomes refractory to treatment. The targeted nanoplex molecules that are disclosed herein, and which carries multimodality imaging reporters together with siRNA and a prodrug enzyme, are useful for theranostic imaging of cancers, including, for example, metastatic PC. The nanoplex molecules of the present invention provide a platform technology toward many cancer subtypes and alternative therapeutic targets. Downregulation of specific pathways using siRNA further provides unique opportunities to target cancer cells selectively while sparing normal tissue. The nanoplex molecule platform described herein has the ability to deliver multiple siRNA. The strategy described herein can be useful to down-regulate multi-drug resistance pathways, or repair enzymes with the goal of increasing the efficacy, safety, and efficiency of chemotherapeutic or irradiation therapies.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

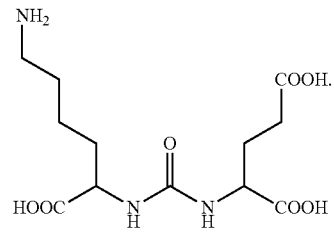 [SMILES: NCCCCC(NC(=O)NC(CCC(=O)O)C(=O)O)C(=O)O]

2. The nanoplex composition of claim 1, wherein the targeting agent is (2-(3-[1-carboxy-5-[7-(2,5-dioxo-pyrrolidin-1-yloxycarbonyl)-heptanoylamino]-pentyl]-ureido)-pentanedioic acid.

3. The nanoplex composition of claim 1, wherein the at least one siRNA is specific for the choline kinase (Chk) enzyme.

4. A pharmaceutical composition comprising one or more nanoplex compositions of claim 1, and a pharmaceutically acceptable carrier.

5. A pharmaceutical composition comprising one or more nanoplex compositions of claim 1, a pharmaceutically active compound, and a pharmaceutically acceptable carrier.

6. A method of modulating expression of a target gene in a host cell or population of cells, wherein the host cell or population of cells express prostate specific membrane anti-

---

---

The invention claimed is:

1. A nanoplex molecule comprising:
   a) a prodrug enzyme portion;
   b) a reporter portion;
   c) an enzyme inhibitor portion; and
   d) a targeting agent;
   wherein,
   the prodrug enzyme portion is the enzyme bacterial cytosine deaminase (bCD);
   the reporter portion is a poly-L-lysine carrier linked to a Cy5.5 dye and a DOTA moiety labeled with $^{111}$In or $Gd^{3+}$ linked to a polyethyleneimine (PEI):poly ethylene glycol (PEG) block co-polymer;
   the enzyme inhibitor portion is at least one siRNA; and
   the targeting agent comprises a prostate specific membrane antigen (PSMA) targeting moiety having the following formula:

gen (PSMA), comprising administering to the cell or population of cells the nanoplex composition of claim 1, or a pharmaceutical composition thereof, in an amount sufficient to modulate target gene expression with the host cell or population of cells.

7. The method of claim 6, wherein the target gene is upregulated in a cancer cell when compared to a non-cancerous cell, wherein the cancer cell has an increased expression of prostate specific membrane antigen (PSMA) relative to the non-cancerous cell.

8. A method for treating a cancer in a subject in need of treatment thereof, the method comprising administering to the subject an effective amount of a nanoplex molecule of claim 1, or a pharmaceutical composition thereof.

9. The method of claim 8, wherein the pharmaceutical composition further comprises a pharmaceutically acceptable carrier.

10. The method of claim 8, wherein the pharmaceutical composition further comprises a second therapeutic agent.

11. The method of claim 8, wherein the cancer is prostate cancer.

12. The method of claim 8, further comprising imaging a target cell or population of cells, wherein the target cell or population of cells express prostate specific membrane antigen (PSMA).

13. The method of claim 12, wherein the imaging is selected from the group consisting of SPECT imaging, PET imaging, MR imaging, and fluorescence imaging.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Homo sapiens

<400> SEQUENCE: 1
caugcuguuc cagugcuccu u                                                  21

<210> SEQ ID NO 2
<211> LENGTH: 21
<212> TYPE: DNA
<213> ORGANISM: Homo sapiens

<400> SEQUENCE: 2
ggagcacugg aacagcaugu u                                                  21
```